(12) United States Patent
Zhang et al.

(10) Patent No.: US 8,646,340 B2
(45) Date of Patent: Feb. 11, 2014

(54) SAMPLING METHOD AND SAMPLING DEVICE

(75) Inventors: Yangtian Zhang, Beijing (CN); Jin Lin, Beijing (CN); Yaoxin Wang, Beijing (CN); Guanxing Li, Beijing (CN); Peng Jiao, Beijing (CN)

(73) Assignee: Nuctech Company Limited, Beijing (CN)

( * ) Notice: Subject to any disclaimer, the term of this patent is extended or adjusted under 35 U.S.C. 154(b) by 351 days.

(21) Appl. No.: 12/746,825

(22) PCT Filed: Dec. 30, 2009

(86) PCT No.: PCT/CN2009/076259
§ 371 (c)(1),
(2), (4) Date: Jun. 8, 2010

(87) PCT Pub. No.: WO2011/000197
PCT Pub. Date: Jan. 6, 2011

(65) Prior Publication Data
US 2011/0126643 A1 Jun. 2, 2011

(30) Foreign Application Priority Data

Jun. 30, 2009 (CN) .......................... 2009 1 0088625

(51) Int. Cl.
*G01N 1/14* (2006.01)
*G01N 1/24* (2006.01)
*G01N 1/22* (2006.01)

(52) U.S. Cl.
CPC ... *G01N 1/22* (2013.01); *G01N 1/24* (2013.01)
USPC .................. 73/863.11; 73/863.81; 73/864

(58) Field of Classification Search
USPC ................... 73/863, 863.01, 863.02, 863.11, 73/863.21, 863.41, 863.51, 863.71, 73/863.81–863.83, 864, 864.81
See application file for complete search history.

(56) References Cited

U.S. PATENT DOCUMENTS

| | | | | |
|---|---|---|---|---|
| 3,748,905 A | * | 7/1973 | Fletcher et al. | 73/863.25 |
| 4,754,655 A | * | 7/1988 | Parker et al. | 73/864.44 |
| 5,663,561 A | * | 9/1997 | Franzen et al. | 250/288 |

(Continued)

FOREIGN PATENT DOCUMENTS

CN   1777799   5/2006

OTHER PUBLICATIONS

Translation of the written opinion from PCT/CN2009/076259 filed on Dec. 30, 2009.*

(Continued)

*Primary Examiner* — David A Rogers
(74) *Attorney, Agent, or Firm* — Westman, Champlin & Koehler, P.A.

(57) ABSTRACT

Disclosed is a sampling method which comprises the steps of: blowing airflow towards a center portion of a sampling surface through a blowing port; and sucking the blown airflow from periphery of the sampling surface through a sucking port, or a sampling method which comprises the steps of: providing a sampling device on a sampling surface, the sampling device being shaped to form a sampling space together with the sampling surface, and the sampling device including a blowing port arranged at the center portion of the sampling device and a sucking port arranged at periphery of the sampling device; blowing airflow towards the sampling surface through the blowing port; and sucking the airflow blown towards the sampling surface through the sucking port so as to collect samples.

14 Claims, 2 Drawing Sheets

(56) References Cited

U.S. PATENT DOCUMENTS

| | | | |
|---|---|---|---|
| 6,354,160 B1* | 3/2002 | Staples et al. | 73/863.12 |
| 6,378,385 B1* | 4/2002 | Bowers | 73/863.12 |
| 6,828,795 B2* | 12/2004 | Krasnobaev et al. | 324/464 |
| 6,867,413 B2 | 3/2005 | Basch et al. | 250/255 |
| 6,888,128 B2* | 5/2005 | Krasnobaev et al. | 250/281 |
| 6,895,804 B2* | 5/2005 | Lovell et al. | 73/31.05 |
| 7,098,672 B2* | 8/2006 | Belyakov et al. | 324/646 |
| 7,299,710 B2* | 11/2007 | Syage | 73/863.12 |
| 7,997,119 B2* | 8/2011 | Wu | 73/31.03 |
| 8,113,069 B2* | 2/2012 | Settles | 73/864.35 |
| 8,161,797 B1* | 4/2012 | Genovese et al. | 73/31.03 |
| 2004/0107782 A1* | 6/2004 | Bradley et al. | 73/864.34 |
| 2007/0068284 A1* | 3/2007 | Castro et al. | 73/863.21 |
| 2007/0086925 A1* | 4/2007 | O'Donnell et al. | 422/100 |
| 2008/0190218 A1* | 8/2008 | Riazanskaia et al. | 73/864 |

OTHER PUBLICATIONS

Office Action from corresponding Chinese Application No. 2009100886257, dated Jun. 30, 2011, 4 pgs.
Search Report from PCT/CN2009/076259, dated Apr. 15, 2010.
Written Opinion from PCT/CN2009/076259, dated Mar. 29, 2010.
Office Action from corresponding Canadian Patent Application No. 2,708,568, dated Nov. 20, 2012.

* cited by examiner

SAMPLING METHOD AND SAMPLING DEVICE

CROSS-REFERENCE TO RELATED APPLICATION

This Application is a Section 371 National Stage Application of International Application No. PCT/CN2009/076259, filed Dec. 30, 2009 and published as WO 2011/000197 A1 on Jan. 6, 2011, the contents of which are hereby incorporated by reference in their entirety.

FIELD OF INVENTION

The present invention relates to detection of dangerous articles, such as narcotic drugs, explosives, chemical warfare agents, industry poisonous agents or the like, more particularly, to a sampling method and a sampling device for the above articles by sucking the same in a form of gaseous or particulate state into a detecting device.

BACKGROUND OF INVENTION

In the security inspection field, it is very important to detect dangerous articles, such as narcotic drugs, explosives, chemical warfare agents, industry poisonous agents. Therefore, various detectors for detecting the above articles have been developed. However, for each kind of detector, samples have to be transferred from a detecting surface of the article into the detector during detecting.

At present, two methods of a suck-type sampling method and a wipe-type sampling method are commonly used. In the wipe-type sampling method, sampling is performed by using a wiping paper to wipe the detecting surface, and then the wiping paper is moved directly into a detector. However, the present application is directed to the suck-type sampling method rather than the wipe-type sampling method. In the suck-type sampling method, sampling is performed directly at the detecting surface by way of sucking, or is performed based on collected samples in advance by way of sucking.

There are mainly two suck-type sampling methods used in existing products or disclosed by published patents. The first method is a direct suction method in which, as shown in FIG. 1, a detecting device sucks air directly from surrounding environment. Because some dangerous articles have viscosity, they tend to adhere to surfaces of an object to be detected. Thus, the direct suction method can only capture volatilized gases or fine particles in a free state. In order to collect the dangerous articles adhered to the surfaces of the object to be detected, a second method is widely used, in which airflow is first blown to raise the particles of the sample; then, the raised particles are sucked into the detecting device, as shown in FIG. 2. Advantageously, the blown airflow is formed of spiral or heated air.

FIG. 2 shows an example of the second method which improves the detecting efficiency; usually, the airflow is blown from peripheral of a sampling device and is sucked at a center part thereof. The above method can be implemented more easily with a sampling device, wherein the inlet of a detecting device is commonly provided at the center part of the sampling device so that the detecting device can be connected directly with the sampling device. However, because an air exit has a large size while the airflow is sucked at the center part, the blowing force of such sampling device is small, which results in a low sampling efficiency.

SUMMARY OF INVENTION

In view of the above, the present invention is made to solve or alleviate at least one of the disadvantages or technical problems in the prior art.

According to an aspect of the present invention, there is provided a sampling method, comprising the steps of: blowing airflow towards a center portion of a sampling surface through a blowing port; and sucking the blown airflow from periphery of the sampling surface through a sucking port.

According to another aspect of the present invention, there is provided a sampling method, comprising the steps of: providing a sampling device on a sampling surface, the sampling device being shaped to form a sampling space together with the sampling surface, and the sampling device including a blowing port arranged at the center portion of the sampling device and a sucking port arranged at periphery of the sampling device; blowing airflow towards the sampling surface through the blowing port; and sucking the airflow blown towards the sampling surface through the sucking port so as to collect samples.

Alternatively, the step of blowing airflow comprises increasing an instantaneous speed of the airflow from the blowing port by means of a volume buffer.

Alternatively, the step of blowing airflow comprises heating the airflow.

Alternatively, the step of blowing airflow comprises adjusting the blowing direction of the airflow from the blowing port with respect to the sampling surface.

Alternatively, the adjusting of the blowing direction is performed by providing a spiral airflow guiding device or a fan within the blowing port.

Alternatively, the blowing port is tapered to increase the speed of the airflow from the blowing port.

Alternatively, the sucking port comprises a plurality of sucking ports, and the blowing port is arranged at a center portion of a polygon formed by the plurality of sucking ports.

Alternatively, the sucking port forms a ring surrounding the periphery of the sampling device, and the blowing port is arranged at a center portion of the ring.

Alternatively, the blowing port extends in a direction which is perpendicular to the sampling surface.

According to further another aspect of the present invention there is provided a sampling device which comprises: a blowing port which blows airflow towards a center portion of a sampling surface; and a sucking port which sucks the blown airflow from periphery of the sampling surface.

According to still another aspect of the present invention, there is provided a sampling device which comprises a housing which is shaped to form a sampling space together with a sampling surface; a blowing port which is provided at a center portion of the housing to blow airflow towards the sampling surface; and a sucking port which is provided at periphery of the housing to suck the airflow blown towards the sampling surface.

Alternatively, the sampling device further comprises a volume buffer which is provided at the upstream of the blowing port in a flowing direction of the to airflow to increase an instantaneous speed of the airflow from the blowing port.

Alternatively, the sampling device further comprises a heater for heating the airflow.

Alternatively, the sampling device further comprises a spiral airflow guiding device which is provided within the blowing port to adjust the blowing direction of the airflow from the blowing port with respect to the sampling surface.

Alternatively, the sampling device further comprises a fan which is provided within, the blowing port to adjust the blowing direction of the airflow from the blowing port with respect to the sampling surface.

Alternatively, the blowing port is tapered to increase the speed of the airflow from the blowing port.

Alternatively, the sucking port comprises a plurality of sucking ports, and the blowing port is arranged at a center portion of a polygon formed by the plurality of sucking ports.

Alternatively, the sucking port forms a ring surrounding the periphery of the sampling device, and the blowing port is arranged at a center portion of the ring.

Alternatively, the blowing port comprises a plurality of blowing ports.

According to the present invention, the blowing device is provided at the center, while the sucking device is provided at the periphery, which may produce the following technical effect.

1. Larger Blowing Force

For the same flow rate, the smaller is the section area of the blowing port, the higher is the speed of the airflow. Thus, the area of the blowing port in the conventional solution where the airflow is blown at the periphery is larger than that of the blowing port in a solution where the airflow is blown at the center according to the present invention; therefore, the present invention can provide a blowing airflow having a higher speed. The blown airflow is used to blow particles of dangerous articles off the detecting surface to which the particles may adhere. According to aerodynamics principle, as for the same particle, blowing force F acting on it is calculated based on the following formula:

$$F = C_d \times \frac{\rho}{2} \times S_d \times v^2$$

wherein parameters in the formula except for the speed v of the airflow are constant, thus, the blowing force F is in direct proportion to the square of v. Therefore, for the same flow rate of the airflow, the solution of the present invention will produce a larger blowing force, compared to the conventional solution.

2. Improved Sampling Efficiency

In the conventional solution, since the area of the blowing port is large, a larger flow rate is needed in order to improve the blowing ability, however, the center portion, which is connected directly to the detecting device, can not provide a sucking airflow having a too large flow rate. Because the flow rate of the blowing airflow is larger than that of the sucking airflow, the particles raised by the blowing airflow supplied from the periphery can not be completely sucked into the detecting device. In addition, some particles raised by the blowing airflow supplied from the periphery may be away from the center portion and therefore it is very difficult to collect them.

With the solution of the present invention in which the airflow is blown at the center portion, a blowing airflow having a higher speed is obtained with a lower flow rate of the blowing airflow, and at the same time, the raised particles move towards the periphery together with the airflow and are captured by the sucking device provided at the periphery, thus, the sampling efficiency is improved.

BRIEF DESCRIPTION OF DRAWINGS

The attached drawings of the present invention will be described below for more complete understanding of the present invention and showing of practicing the present invention, wherein.

DETAILED DESCRIPTION OF EMBODIMENTS

Exemplary embodiments of the present disclosure will be described hereinafter in detail with reference to the attached drawings. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

Sampling Method

Figure 1:
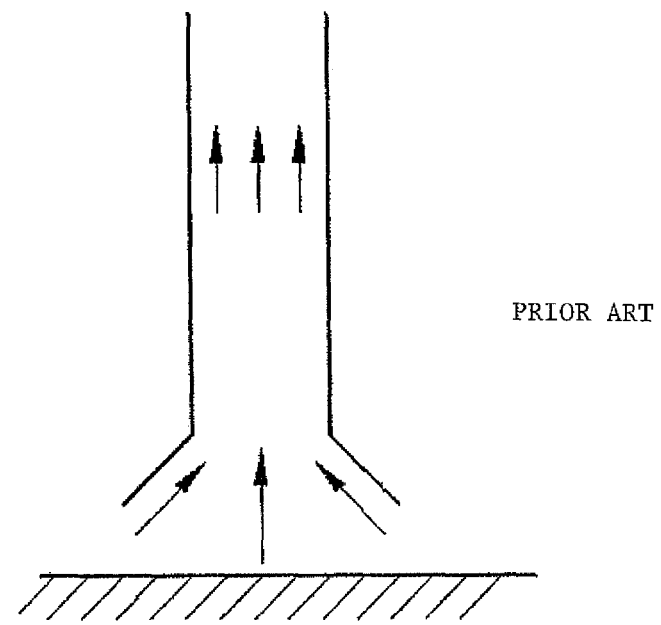
FIG. 1 is a schematic view of a direct air-suction method of the prior art.
Figure 2:
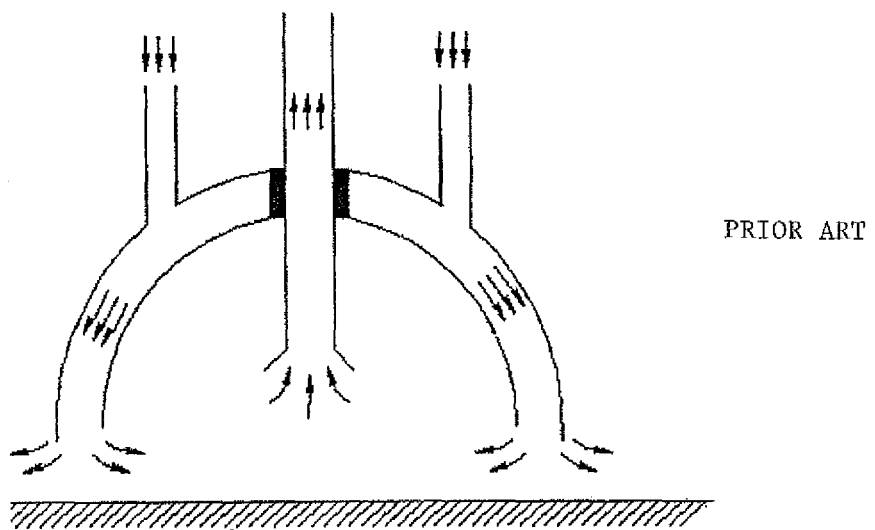
FIG. 2 is a schematic view showing an air passage solution of the prior art in which the air is blown from the periphery and is sucked in the center portion.
Figure 3:
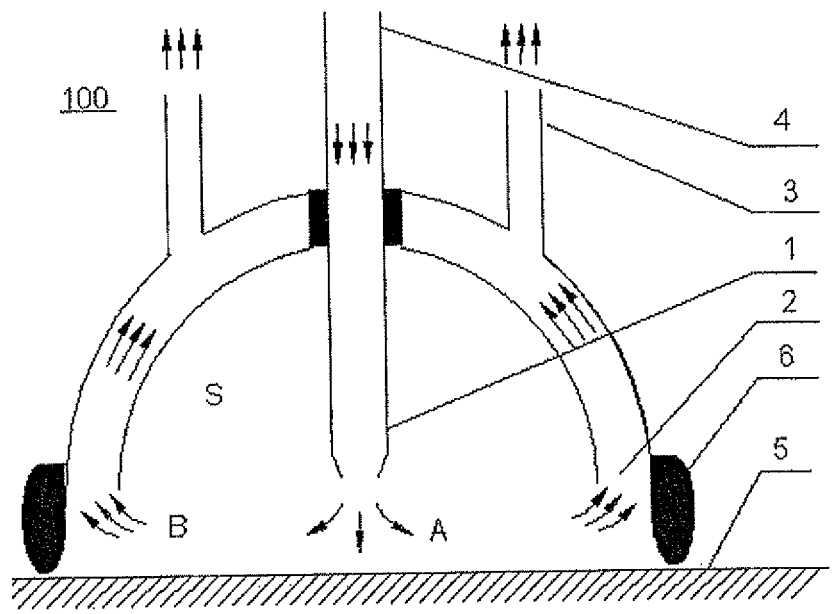
FIG. 3 is a schematic view showing an air passage solution according to one embodiment of the present invention in which the air is blown from the center portion while is sucked in the periphery.

Refer to FIG. 3, a sampling method according to the present invention comprises the steps of: blowing airflow towards a center portion of a sampling surface 5 through a blowing port 1, as shown by the arrow A; and sucking the blown airflow from periphery of the sampling surface 5 through a sucking port 2, as shown by the arrow B.

Also refer to FIG. 3, another sampling method according to the present invention comprises the steps of: providing a sampling device 100 on a sampling surface 5, the sampling device 100 being shaped to form a sampling space S together with the sampling surface 5, and the sampling device 100 including a blowing port 1 arranged at the center portion of the sampling device 100 and a sucking port 2 arranged at periphery of the sampling device 100; blowing airflow towards the sampling surface through the blowing port, as shown by the arrow A; and sucking the airflow blown towards the sampling surface through the sucking port so as to collect samples, as shown by the arrow B.

As known in the art, the blowing port 1 is communicated with a blowing air source (not shown) through an inlet 4, and the sucking port 2 is communicated with a detecting device (not shown) through an outlet 3.

In the above sampling methods, the step of blowing airflow comprises increasing an instantaneous speed of the airflow from the blowing port by means of a volume buffer (not shown) and/or the step of blowing airflow comprises heating the airflow. In an embodiment, the volume buffer may be provided at the upstream of the blowing port 1, for example, when the air pressure in the volume buffer reaches a predetermined value, the air in the volume buffer is blown at a high speed towards the sampling surface 5 via the blowing port 5, then the volume buffer begins to re-accumulate air therein. Thus, the blowing airflow is intermittent; however, a high speed is obtained. If the blowing air is heated before blowing towards the sampling surface, the volatilization of the dangerous articles at the sampling surface is expedited or the adhering of the articles to the sampling surface is weakened, which results in an improved sampling precision.

Figure 4:
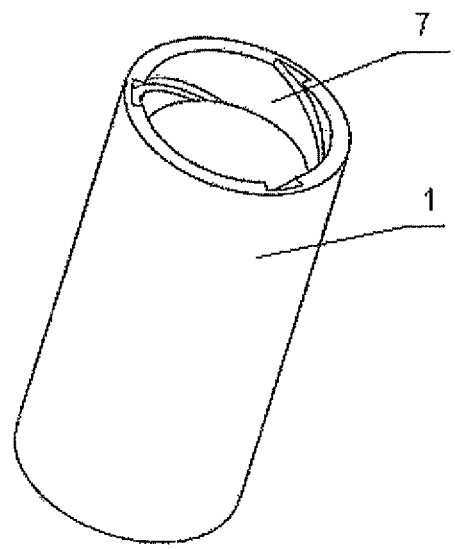
FIG. 4 is a schematic view a spiral airflow guiding device according to one embodiment of the present invention.

In the above sampling methods, the step of blowing airflow comprises adjusting the blowing direction of the airflow from the blowing port 1 with respect to the sampling surface 5. Advantageously, the adjusting of the blowing direction is performed by providing a spiral airflow guiding device 7 (referring to FIG. 4) within the blowing port 1, or the adjusting of the blowing direction is performed by providing a fan (not shown) within the blowing port 1. For example, the blowing airflow is swirled above the sampling surface 5 by using the spiral airflow guiding device 7 or the fan, so that the blowing ability of the airflow is enhanced.

Advantageously, the blowing port 1 is tapered to increase the speed of the airflow from the blowing port 1. For instance, the blowing port 1 is formed as a nozzle.

Next, the arrangement of the sucking port 2 will be described. The sampling device 100 may comprise a plurality of sucking ports 2, and in this case the blowing port 1 can be arranged at a center portion of a polygon formed by the plurality of sucking ports. Alternatively, the sucking port 2 may form a ring surrounding the periphery of the sampling device 100, and the blowing port 1 is arranged at a center portion of the ring.

In addition, in order to improve the disturbance ability of the blowing airflow to the samples on the sampling surface 5, the blowing port 1 may extend in a direction which is perpendicular to the sampling surface.

In order to improve the sucking efficiency, for example, to prevent or restrict receiving air outside of the sampling device, a skirt portion 6 is provided at the periphery of the sampling device 100 to seal the sampling space S.

Sampling Device

Refer to FIG. 3, a sampling device 100 according to one embodiment of the present invention comprises: a blowing port 1 which blows airflow towards a center portion of a sampling surface 5, referring to the arrow A; and a sucking port 2 which sucks the blown airflow from periphery of the sampling surface 5, referring to the arrow B.

Also refer to FIG. 3, a sampling device 100 according to another embodiment of the present invention comprises a housing 10 which is shaped to form a sampling space S together with a sampling surface 5; a blowing port 1 which is provided at a center portion of the housing 10 to blow airflow towards the sampling surface, referring to the arrow A; and a sucking port 2 which is provided at periphery of the housing 10 to suck the airflow blown towards the sampling surface, referring to the arrow B.

As known in the art, the blowing port 1 is communicated with a blowing air source (not shown) through an inlet 4, and the sucking port 2 is communicated with a detecting device (not shown) through an outlet 3.

The above sampling devices 100 may further comprise a volume buffer (not shown) which is provided at the upstream of the blowing port 1 in a flowing direction of the airflow to increase an instantaneous speed of the airflow from the blowing port 1. For example, when the air pressure in the volume buffer reaches a predetermined value, the air in the volume buffer is blown at a high speed towards the sampling surface 5 via the blowing port 5, then the volume buffer begins to re-accumulate air therein. Thus, the blowing airflow is intermittent; however, a high speed is obtained.

The above sampling devices 100 may further comprise a heater (not shown) for heating the airflow. For instance, the heater may be provided directly within the blowing port 1. If the blowing air is heated before blowing towards the sampling surface, the volatilization of the dangerous articles at the sampling surface is expedited or the adhering of the articles to the sampling surface is weakened, which results in an improved sampling precision.

The above sampling devices 100 may further comprise a spiral airflow guiding device 7 (referring to FIG. 4) which is provided within the blowing port 1 to adjust the blowing direction of the airflow from the blowing port 1 with respect to the sampling surface 5. In an embodiment, the above sampling devices 100 may further comprise a fan or other guiding member (not shown) which is provided within the blowing port 1 to adjust the blowing direction of the airflow from the blowing port 1 with respect to the sampling surface 5. For example, the blowing airflow is swirled above the sampling surface 5 by using the spiral airflow guiding device 7 or the fan, so that the blowing ability of the airflow is enhanced.

Advantageously, the blowing port 1 is tapered to increase the speed of the airflow from the blowing port 1. For instance, the blowing port 1 is formed as a nozzle. Though not shown, the sampling device 100 may comprise a plurality of blowing ports 1.

Next, the arrangement of the sucking port 2 will be described. The sampling device 100 may comprise a plurality of sucking ports 2, and in this case the blowing port 1 can be arranged at a center portion of a polygon formed by the plurality of sucking ports. Alternatively, the sucking port 2 may form a ring surrounding the periphery of the sampling device, and the blowing port 1 is arranged at a center portion of the ring.

In the sampling devices 100, in order to improve the disturbance ability of the blowing airflow to the samples on the sampling surface 5, the blowing port 1 may extend in a direction which is perpendicular to the sampling surface.

In order to improve the sucking efficiency, for example, to prevent or restrict receiving air outside of the sampling device, a skirt portion 6 is provided at the periphery of the sampling device 100 to seal the sampling space S.

Although a few embodiments have been shown and described, it would be appreciated by those of ordinary skill in the art that changes and variants may be made in these embodiments without departing from the principles and spirit of the invention, the scope of which is defined in the claimed and their equivalents.

The invention claimed is:

1. A sampling method, comprising the steps of:
   blowing airflow towards a center portion of a sampling surface through a blowing port provided above the central portion of the sampling surface; and
   sucking the blown airflow from periphery of the sampling surface through a sucking port provided along the periphery of the sampling surface,
   wherein the step of blowing airflow comprises adjusting the blowing direction of the airflow from the blowing port with respect to the sampling surface, and the adjusting of the blowing direction is performed by providing a spiral airflow guiding device within the blowing port or by providing a fan within the blowing port.

2. The sampling method according to claim 1, wherein the step of blowing airflow comprises increasing an instantaneous speed of the airflow from the blowing port by means of a volume buffer.

3. The sampling method according to claim 1, wherein the step of blowing airflow comprises heating the airflow.

4. The sampling method according to claim 1, wherein the blowing port is tapered to increase the speed of the airflow from the blowing port.

5. The sampling method according to claim 1, wherein the sucking port comprises a plurality of sucking ports, and the blowing port is arranged at a center portion of a polygon formed by the plurality of sucking ports.

6. The sampling method according to claim 1, wherein the sucking port forms a ring surrounding the periphery of the sampling device, and the blowing port is arranged at a center portion of the ring.

7. The sampling method according to claim 1, wherein
the blowing port extends in a direction which is perpendicular to the sampling surface.

8. A sampling device comprising:
a blowing port which blows airflow towards a center portion of a sampling surface, wherein the blowing port is provided only above the central portion of the sampling surface; and
a sucking port which sucks the blown airflow from periphery of the sampling surface, wherein the sucking port is provided only along the periphery of the sampling surface,
wherein a spiral airflow guiding device or a fan is provided within the blowing port to adjust the blowing direction of the airflow from the blowing port with respect to the sampling surface.

9. The sampling device according to claim 8, further comprising a volume buffer which is provided at the upstream of the blowing port in a flowing direction of the airflow to increase an instantaneous speed of the airflow from the blowing port.

10. The sampling device according to claim 8, further comprising
a heater for heating the airflow.

11. The sampling device according to claim 8, wherein
the blowing port is tapered to increase the speed of the airflow from the blowing port.

12. The sampling device according to claim 8, wherein
the sucking port comprises a plurality of sucking ports, and the blowing port is arranged at a center portion of a polygon formed by the plurality of sucking ports.

13. The sampling device according to claim 8, wherein
the sucking port forms a ring surrounding the periphery of the sampling device, and the blowing port is arranged at a center portion of the ring.

14. The sampling device according to claim 8, wherein
the blowing port comprises a plurality of blowing ports.

* * * * *